US008924864B2

(12) United States Patent
Mariotti et al.

(10) Patent No.: US 8,924,864 B2
(45) Date of Patent: Dec. 30, 2014

(54) SYSTEM AND METHOD FOR COLLABORATIVELY COMMUNICATING ON IMAGES AND SAVING THOSE COMMUNICATIONS AND IMAGES IN A STANDARD KNOWN FORMAT

(75) Inventors: Mark Mariotti, Westford, MA (US); Anthony Molinari, Grafton, MA (US); James Smurro, San Clemente, CA (US)

(73) Assignee: Foresight Imaging LLC

( * ) Notice: Subject to any disclaimer, the term of this patent is extended or adjusted under 35 U.S.C. 154(b) by 556 days.

(21) Appl. No.: 12/592,328

(22) Filed: Nov. 23, 2009

(65) Prior Publication Data
US 2011/0126127 A1    May 26, 2011

(51) Int. Cl.
*G06F 3/00* (2006.01)
*H04M 7/00* (2006.01)
*G06F 19/00* (2011.01)

(52) U.S. Cl.
CPC .......... *H04M 7/0027* (2013.01); *G06F 19/321* (2013.01); *G06F 19/3425* (2013.01)
USPC .......................................... 715/753; 715/756

(58) Field of Classification Search
CPC .............. G06F 19/321; G06F 19/3418; G06F 19/3425; G06F 17/241; G06Q 50/24; G06Q 50/22; G06Q 10/10; H04L 67/02; H04L 12/1822; A61B 5/0002; A61B 5/055; A61B 8/461
USPC ....................................................... 715/753
See application file for complete search history.

(56) References Cited

U.S. PATENT DOCUMENTS

| | | | |
|---|---|---|---|
| 5,838,914 A | 11/1998 | Carleton et al. | |
| 6,105,055 A * | 8/2000 | Pizano et al. | 709/204 |
| 6,507,865 B1 | 1/2003 | Hanson et al. | |
| 6,532,218 B1 | 3/2003 | Shaffer et al. | |
| 6,556,724 B1 * | 4/2003 | Chang et al. | 382/299 |
| 6,662,210 B1 | 12/2003 | Carleton et al. | |
| 6,809,749 B1 * | 10/2004 | Chen et al. | 715/753 |
| 7,257,832 B2 * | 8/2007 | Beane et al. | 725/105 |
| 7,310,657 B2 | 12/2007 | Nakamura | |
| 7,366,992 B2 * | 4/2008 | Thomas, III | 715/764 |
| 7,411,693 B2 * | 8/2008 | Loukipoudis et al. | 358/1.15 |
| 7,668,835 B2 * | 2/2010 | Judd et al. | 707/999.01 |
| 7,933,472 B1 * | 4/2011 | Canessa et al. | 382/305 |
| 7,953,608 B2 * | 5/2011 | McCallie et al. | 705/2 |
| 7,983,933 B2 * | 7/2011 | Karkanias et al. | 705/2 |
| 8,014,576 B2 * | 9/2011 | Collins et al. | 382/128 |
| 8,015,032 B2 * | 9/2011 | Keen | 705/3 |
| 8,065,166 B2 * | 11/2011 | Maresh et al. | 705/3 |

(Continued)

*Primary Examiner* — Omar Abdul-Ali
*Assistant Examiner* — Phoebe Pan
(74) *Attorney, Agent, or Firm* — Michael Leccese

(57) ABSTRACT

A network apparatus system and method of use adapted for viewing, illustrating, consulting and collaborating on medical images and saving images and illustrations in acceptable DICOM format. Specifically, a Consultant Client or a plurality of Consultant Clients having the capability to view still and streaming video medical images, then illustrating over those images with the ability to save those images. Also a Collaborator Client, a person user or a plurality of Collaborator Clients having the ability to remotely view streaming or still medical images and illustrating over those images. The Collaborator Clients can draw, telestrate and annotate over those images with the ability to save those images. The Collaborator Client also has the ability to work in partnership with other Collaborator Clients, each Collaborator Client viewing the same medical image and each illustrating on the image and each being able to view all users illustrations and medical image simultaneously.

5 Claims, 12 Drawing Sheets

(56) References Cited

U.S. PATENT DOCUMENTS

| | | |
|---|---|---|
| 8,099,307 B2 * | 1/2012 | Maresh et al. .................... 705/3 |
| 2001/0031997 A1 * | 10/2001 | Lee .................. 607/59 |
| 2002/0049786 A1 * | 4/2002 | Bibliowicz et al. ........... 707/511 |
| 2002/0184325 A1 * | 12/2002 | Killcommons et al. ....... 709/206 |
| 2003/0031992 A1 * | 2/2003 | Laferriere et al. ............ 434/262 |
| 2003/0105650 A1 * | 6/2003 | Lombardo et al. ................. 705/2 |
| 2004/0054760 A1 * | 3/2004 | Ewing et al. .................. 709/219 |
| 2004/0237032 A1 * | 11/2004 | Miele et al. .................... 715/512 |
| 2005/0055642 A1 * | 3/2005 | Chen et al. .................... 715/753 |
| 2005/0063575 A1 * | 3/2005 | Ma et al. ...................... 382/128 |
| 2005/0251009 A1 * | 11/2005 | Morita et al. ................. 600/407 |
| 2006/0034521 A1 * | 2/2006 | Lindmark et al. ............ 382/232 |
| 2006/0122482 A1 * | 6/2006 | Mariotti et al. ............... 600/407 |
| 2006/0149601 A1 * | 7/2006 | Langhofer et al. ............... 705/3 |
| 2006/0177114 A1 * | 8/2006 | Tongdee et al. .............. 382/128 |
| 2006/0236247 A1 * | 10/2006 | Morita et al. .................. 715/733 |
| 2007/0014455 A1 * | 1/2007 | Howerton, Jr. .............. 382/128 |
| 2007/0061393 A1 * | 3/2007 | Moore .......................... 709/219 |
| 2007/0106537 A1 * | 5/2007 | Moore ............................... 705/3 |
| 2007/0106633 A1 * | 5/2007 | Reiner .............................. 707/1 |
| 2007/0106750 A1 * | 5/2007 | Moore .......................... 709/217 |
| 2007/0106751 A1 * | 5/2007 | Moore .......................... 709/217 |
| 2007/0106752 A1 * | 5/2007 | Moore .......................... 709/217 |
| 2007/0106753 A1 * | 5/2007 | Moore .......................... 709/217 |
| 2007/0106754 A1 * | 5/2007 | Moore .......................... 709/217 |
| 2007/0168461 A1 * | 7/2007 | Moore .......................... 709/217 |
| 2007/0199031 A1 * | 8/2007 | Nemirofsky et al. ............ 725/88 |
| 2007/0258638 A1 * | 11/2007 | Howerton, Jr. ................. 382/154 |
| 2007/0288264 A1 * | 12/2007 | Brown et al. ..................... 705/2 |
| 2008/0021740 A1 * | 1/2008 | Beane et al. ...................... 705/3 |
| 2008/0044069 A1 * | 2/2008 | DuGal .......................... 382/128 |
| 2008/0310816 A1 * | 12/2008 | Allen et al. ...................... 386/52 |
| 2009/0210801 A1 * | 8/2009 | Bakir et al. .................... 715/753 |
| 2010/0042653 A1 * | 2/2010 | Krishnan et al. ........... 707/104.1 |
| 2010/0119164 A1 * | 5/2010 | Singhal et al. ................ 382/233 |
| 2010/0169269 A1 * | 7/2010 | Chandrasekaran ........... 707/608 |
| 2010/0267359 A1 * | 10/2010 | Gyllensvaan ............... 455/404.1 |
| 2011/0029326 A1 * | 2/2011 | Venon ............................... 705/3 |
| 2011/0106557 A1 * | 5/2011 | Gazula ............................. 705/3 |
| 2011/0150420 A1 * | 6/2011 | Cordonnier ................... 386/241 |
| 2013/0173439 A1 * | 7/2013 | Christiansen .................... 705/34 |
| 2013/0251233 A1 * | 9/2013 | Yang et al. ..................... 382/132 |

* cited by examiner

Collaboration Sessions:

| Session ID | Initiated By | Start Time | End Time | Media Name |
|---|---|---|---|---|
| 10122009153130812 | Mike Jones | 10/12/2009 3:26:22PM | | img_8142009५249.jpeg |

[End Session] [View Session]

Participant Information:

| First Name | Last Name | Join Time | End Time | Participant Status | Annotation Control | Video Control |
|---|---|---|---|---|---|---|
| Mike | Jones | 10/12/2009 3:26:22PM | | Started Session | ☑ | ☑ |
| Bill | Joy | 10/12/2009 3:26:27PM | | Joined Session | ☑ | ☐ |

[Add Participant] [Update Controls]

Initiate Collaboration Session [Browse Media] [Collaborate]
Media Path: [_____]

[Streams] [Sessions] [Viewer] [Studies]

| UserID | First Name | Last Name | EmailID | Roles | Status | Online Status |
|---|---|---|---|---|---|---|
| admin | Ken | Thompson | Test4sight@gmail.com | Administrator | Active | Available |
| client1 | Bill | Joy | Client1@gmail.com | Orlando | Active | Available |
| client2 | Will | Smith | Client2@gmail.com | Orlando | Active | Unavailable |
| initiator | Mike | Jones | initiator@gmail.com | Miami | Active | Available |
| miami | Denis | Ritchie | test4sight@gmail.com | Miami | Active | Unavailable |
| miami1 | mFirst1 | mLast1 | miami1@gmail.com | Miami | Inactive | Unavailable |
| miami2 | mFirst2 | mLast2 | miami2@gmail.com | Administrator | Active | Available |
| test | Jim | Carbett | test4sight@gmail.com | Administrator | Active | Unavailable |

SYSTEM AND METHOD FOR COLLABORATIVELY COMMUNICATING ON IMAGES AND SAVING THOSE COMMUNICATIONS AND IMAGES IN A STANDARD KNOWN FORMAT

FIELD

The invention relates generally to a medical apparatus and method of using the same for receiving and transmitting medical images and audio signals in real time allowing operators to concurrently annotate and telestrate in real time. The invention acquires medical images and through an input device, the operators electronically concurrently collaborate, generally by telestrating, annotating, sketching image overlaying on a captured medical image and can save those images in a DICOM format.

BACKGROUND

This invention relates to a medical imaging real time viewing videoconferencing system, more particularly an apparatus and method of using said medical imaging videoconferencing system with multiple input operators or participant clients viewing each other's inputs collaboratively and concurrently.

Videoconferencing systems are becoming more commonly used to conduct meetings and share information, including in the medical field. Participants are typically geographically separated and wish to share ideas and thoughts as they participate in the conference. With such a videoconferencing system, audio and video signals are transmitted over a communication link, such as telephonic, to be reproduced at a remote videoconferencing system so the parties can see and hear each other. In many cases, the videoconferencing systems can support video images allowing each party to view moving camera images, as well as other screen displays. Videoconferencing systems are used in many different ways. Some of the most common is to share computer graphic presentations, such as a POWERPOINT® slide presentation where a user shares his or her slide presentation with others in the conference. The parties can also share video images. The operator uses the available conferencing system and Super Video Graphic Array (SVGA) as a method of viewing these video signals to document and provide camera images on the user's computer or laptop.

Past videoconferencing systems have many disadvantages, including but not limited to, if a participant has a question on a slide or aspect of the presentation, the presenter must control the images to scroll back to the location in question and must toggle through the slide presentation to answer the participants' question. Also, in most conferencing systems, the presenter has control over the presentation, and the participant has no control over what other participants can view.

Recently many inventors have seen the need to allow a plurality of clients or users to collectively collaborate on presented work. These systems allow two or more users of the internet to move or modify Hyper Text Markup Language (HTML) documents with referring to the same. These systems work with browsers and web sharing managers provided in the shared client computer system of a source and receiver, and are constructed in such a manner that the web sharing manager of the shared client computer system of the receiver can receive the event message of the source from the web sharing manager of that source. Accordingly the event message is shared by the source and receiver, and the displaying and controlling of the same web page are simultaneously realized on the shared client computer system. Even further still, as incorporated by reference U.S. Pat. No. 7,310,657 to Nakamura describing in summary, a computer system comprising a plurality of user systems connected to each other being adapted to display a work area on a display screen, alternatively a plurality of users' systems connected to each other though a computer network. In Nakamura user systems include: collaboration work controller having a user management table for registering a node identification code given for each of the user systems and owner identifier related to the node identification code, and an object management table for registering object information related to the node identification code; and an obtainer for obtaining, based on an event entry for an object, the node identification code related to the object by referring to the object management table, obtaining the owner identified related to the obtained node identification code by referring to the user management table, and displaying the object on the screen in the manner that the obtained owner identifier can be discriminated from owner identifiers of other objects. Nakamura shows a display screen where users are participating and collaborating in work drawing annotations simultaneously. The owner identifier identifies the user for each object the owner identifier is displayed to the user watching the display screen with the entry (drawing) of the object from the other user. In other words the owner can be identified; it is possible to identify the owner of the object of the collaborative work easily. Each system runs from each system and does not work from a server but merely each computer runs individually over a network.

However, in past systems the computer arrangement can be summarized as a plurality of users systems connected to each other, each being adapted to display a work area on a display screen or connected through a computer network. Collaboration of work is done on each system by use of a management table for registered node identification codes given for each system user. That is, every computer system, or one system, requires (as in Nakamura) storage of collaboration user identifier in at least one of the user's computer system. The inventor of this novel concurrently collaborative communications device and method for use has improved upon the past art by allowing a server master control allowing for faster and more efficient performance, as well as allowing for a medical Digital Imaging and Communications in Medicine, hereinafter referred to as DICOM, environment. As this invention approves upon and applies in a concurrently collaborative environment and allows for each user to collaborate simultaneously with all users viewing every other users' work product, as the work product is being created, all coincident with image including video, and audio, wherein the medical image together with based on a server and the illustrations are appended to that image.

The traditional way of capturing an image on a medical imaging apparatus commonly called a modality, generally consisted of an operator or technician first conducting a scan. Then, using the modality to save the image, in still or motion video format, into the modality memory or into a main image storage database. Soon afterward, perhaps downloading the image into a hospital database such-as a PACS system, Picture Archiving and Communications System, hereinafter referred to as (PACS) or PACS server, or medical imaging archives for storage and later retrieval. Hereinafter referred generically as PACS. PACS can be further defined by a storage and management system for medical images. Typically, pertaining to the medical field, images such as x-rays, MRI's and CAT scans require a greater amount of storage than other images in other industries. The doctor would then access the PACS system to retrieve the image, the doctor at that time would call up the image, view and review the image, and conceivably develop a diagnosis based on the information from the image. This system imagery is viewed by a user and diagnosis made without image delay and the user accomplishes all these tasks in real time. Real time referring to events simulated by a computer at the same speed that they would normally occur in real life. In graphics animation, for example, a real time program (such as this inventor's system) would display objects moving across the display at the same time they would actually move, or in the case of this invention, a collaborator client views the image in real time and collaborates from client to client with no perceivable delay to any client. The illustrated embodiment is comprised of three essential components (FIG. 1,2): one called Tele Medicine Imagine Management System (TIMS) Server, another called the TIMS Collaborator, and a third called the TIMS Streamer. The TIMS Server is a computer that manages users, security, channels and sessions within the TIMS Collaborator™ System (i.e. this invention described herein) allows for multiple users in multiple locations to concurrently collaborate on the images, each user to input highlighted graphic electronic traces and annotations over the medical image is also a system that allows one or more users located remotely to the imaging modality, to analyze, discuss, and save such analysis or discuss in a clinically relevant manner. Each is able to view, and comment on each of the users input concurrently in real time. The TIMS Streamer server is a device that processes any video output from a video source into a stream. A stream is defined as at least one image frame that defines a time progression of output from a video source.

In one embodiment, the TIMS Server provides the real-time video and audio communication, as well as a method of recording, transmitting and saving images in a single file format structure, including as specified in DICOM Standard. DICOM is a medical imaging standard common in the medical industry. DICOM can also be defined as a standard in the field of medical informatics for exchanging digital information between medical imaging equipment (such as radiological imaging) and ensuring interoperability with other systems. DICOM, including protocols for device communication over a network, syntax and semantics for commands and associated information that can be exchanged using protocols, a set of storage services and devices claiming conformation to the standard, as well as file format and medical directory structures to facilitate access to images and related information stored on media that shares information. The embodiment can serve as the connection point between any medical imaging modality and a hospital PACS, medical archive or other image repository. One component of this invention, the TIMS Server, is able to connect DICOM equipment and older non-DICOM equipment to a hospital network, allowing imaging studies to be stored and saved. The TIMS Collaborator™ System, this invention described herein, briefly described as a trace overlay and annotation system that users can collaborate with each other in real time, each viewing each other's object inputs and those object inputs can be encapsulated and saved in a single file format structure, including as specified in DICOM Standard, in PACS, in a DICOM compliant image archive, or in other image repositories.

The inventor has developed a novel and simple network system apparatus and method of using the same, to allow a group of persons to concurrently collaborate on a computer system, with each participant viewing each other's telestrations, drawings, and annotations and saving them together with streaming imagery data, and relevant imagery metadata, including appended imagery metadata and saving them together in a single file format structure as may be required by standards for clinical documentation or medical records storage, including as specified in the DICOM Standard.

The invention relates generally to a multimedia collaborative conferencing system and method of using the same for generating input illustrations, which include telestrations, drawings and annotations on medical images concurrently with other users and saving the participant client input illustrations with streaming imagery data, and relevant imagery metadata, including appended imagery metadata in a single file format structure, including as specified in the DICOM Standard. The network system apparatus in this invention, is the TIMS Collaborator™ System. It is comprised of three essential components, one called the TIMs Server, another called the Collaborator Client, and a third called the TIMS Streamer. The TIMS Streamer includes a medical image acquisition system adapted for receiving and transmitting medical images, constructed from, a computer having communications capability adapted for acquisition and transmission of a plurality of medical imaging and video signals. Wherein the medical image and video signals are acquired at the medical device's native resolutions, transmitting the signals at their native resolutions and native frame rates to a receiving device, receiving the medical imaging video signals in analog or digital form, and if required, compressing and scaling the signal, converting the signal to digital form for transmission, and transmitting the digital signals using secure encryption protocols to a display device. The TIMS Streamer is capable of concurrently acquiring signals from a plurality of medical imaging systems, as depicted in FIG. 1, including but not limited to, ultrasound, Computer Tomography (CT) scan, fluoroscopy, endoscopy, magnetic resonance imaging, nuclear medicine, echocardiogram ultrasound and microscopy. Medical imaging equipment is also referred to as modalities. A more complete list of sources for DICOM imagery streams can be found in the DICOM Standard [PS 3.3 Part 3: Information Object definitions.], which include video (imaging), audio (waveform), and clinical documents (structured reports).

The TIMS Streamer can also receive the video image signal from a plurality of video sources, including but not limited to, S-video, composite color and monochrome, component red blue green video (RGB, three additive primary colors), Digital Visual Interface (DVI), any video transport protocol including digital and analog protocols, high definition multimedia interface (HDMI, compact audio video interface uncompressed digital data), serial digital interface (SDI), and DICOM video in their native, enhanced or reduced resolutions or their native, enhanced or reduced frame rates. The component, known in this invention as the TIMS Server, manages the communication between all acquisition systems (TIMS Streamers), between all users (Collaborator Clients), between the hospital site server, located on site or remotely, that stores the hospital's images, and the hospital network in both local area and wide area configurations. The TIMS Server manages the real time streaming imagery data acquired from the TIMS Streamers, and archived imagery retrieved in a predetermined digital single file format structure, including as specified in DICOM Standard. A participant or user computer can be defined as typically made of several components such as a main circuit board assembly having a central processing unit, memory storage to store programs and files, other storage devices such as hard drives, and portable memory storage, a power supply, a sound and video circuit board assembly, a display, and an input device such as a keyboard, mouse, stylus pen and the like allowing control of the computer graphics user interface display, where any two or more of such components may be physically integrated or may be separate. In one depiction, a remote location communicates with the networked computer, for the purpose of collaborating and conferencing with medical streaming imagery data.

An apparatus and method for using the same for concurrent collaboration between users, collaborating by video, audio, telestrations and annotations, including collaborating on medical images that are typically accessed on a storage server database, imaging archives, or continuous streaming video. The streamer server is continuously streams images to the TIMS server. Any number of clients can request information from the TIMS server. Each client in a conference with another or other clients can view all the clients object inputs as they occur. A client includes a user, typically a person who has interest in using the system for medical review and diagnosis of patient image data. The TIMS server keeps track of all steaming devices that are available and show it as such to the consultant clients and collaborator clients, and any conduit between. The TIMS server provides continuity with the PACS system, and stores information on all clients The TIMS server includes: a manager, this component controls the streaming requests to the streamer; server and also manage authorization and authentication tasks for access and privileges; the TIMS server, an administrative interface that manages users information, roles, session information, TIMS server configuration, streamer server configuration, web services wherein the web service interacts with the consultant client and collaborator client, performing such services as-sending studies to PACS, retrieving studies from PACS, retrieving study and patient information from a DICOM modality worklist utility (DMWL), sending media for a collaboration session to the client; participants of that conference, PACS server configuration, text chat information; a DICOM send service, wherein the DICOM send service retrieves the list of studies from the PACS server and sends the studies to the clients. A study is defined as medical images and patient data combined. DICOM Modality Worklist is defined as a software utility that invokes DICOM query and retrieve functionality which enables imaging equipment (e.g. medical modalities) to query medical image repositories, including but not limited to PACS, and obtains details of patient and scheduled examinations electronically, including patient demographics and study data, avoiding the need to type patient information multiple times (FIG. 10).

The TIMS server also manages all the illustration overlays, specifically, the entire client sketches, drawings, telestrations and annotations. Illustrations, also known as collaborant annotations are defined herein as any user input such as but not limited to drawings, sketches, telestrations, voice annotations, letter character text and numeric character text (FIG. 7). All illustrations are managed by the TIMS server based on a file sharing scheme where new illustrations keep getting appended to the file on the TIMS server. Only a copy of the populated file is locally maintained on each client's computer. This approach of appending files on the TIMS server significantly improves performance and reduces image wait time, unlike the prior art approach of each computer having to update the image file and send it. This process of multi layer multi user illustration appending and updating on the TIMS server any underlying image, including video, without sacrificing bandwidth is novel to this invention. Appending the files to the server periodically can be performed in a synchronous manner or asynchronous manner. Moving images with illustrations back and forth from a computer to a server, results in losing illustration quality or consuming more bandwidth. However, this novel invention appends only the illustration file to the TIMS server. All client computers use a local registration method process, local to the frame used for viewing. Each client is able to use a scalable window so all illustrations are ratio metric based on the underlying image aspect ratio. Therefore, all the illustrations always point to the part of the window and image as originally intended, regardless of window size on the clients computer display. For example, from the TIMS server, the streaming images and the client's computers that are capturing those images are used in a collaborative session. First, the files are distributed to all the participating clients. A central frame counter originating in the client computer of the person who has play/pause control merely issues frame synchronization commands to synchronize the stream on all client's systems. This method significantly reduces bandwidth and improves responsiveness of the-system. Synchronization can further be optimized by periodic synchronization signals used by the session initiator/controller such that every so many frames are confirmed to be synchronized. The client computer also sends a synchronized command whenever the computer image is paused, thus ensuring that the same frame is available to all participating clients by broadcasting the pause frame number along with the pause command to all participating clients. Client participants can receive video streams directly from the streamer server using a local area network. The invention can also detect if a user has low bandwidth and can compensate by only sending selected frames of the image to that user. or if initiator pauses on a frame can send that frame to users. An example, with low bandwidth of this is that the server sends every third or fifth frame of a video to one client so that client does not have any perceivable delay due to low bandwidth. However, client participants using the internet must receive all streams from the TIMS server. This is done to add a level of security so images do not go over the internet without encryption.

Participants can take several roles. The users can view real time streaming; video, view selected real time streaming video capture real still or motion video; view in real time captured streaming video; add multiple channels dynamically (FIG. 4). In addition, Consultant Client application is a collaborative, interactive synchronous or asynchronous media annotation-system, which will be used in medical files, used to enable users to collaborate and interact on archived medical images for clinical review and discussions and deciding on relevant medical procedures. The Collaborator Client can perform all of the functions of the Consultant Client, as well as communicate with another or other participating clients, by adding annotations in text or drawing form, text chat, query, save, and retrieve studies to and from PACS, and retrieve study and patient information from a DICOM Modality WorkList server (DMWL).

Communication between components is summarized as follows: The client (either the Consultant Client or-Collaborator Client views a stream to the TIMS server (FIG. 9). The TIMS server sends that request to the streamer server. The streamer server provides the stream to the requesting client directly, if connected through a local area network or through the TIMS server, if connected to the internet. When the client sends a request to stop the stream, the TIMS server notifies the streamer server to stop streaming to that client. TIMS server communication with a PACS server is as follows: the client sends a request to the TIMS server to store and/or retrieve studies from-the PACS server. The DICOM send service either retrieves the file and sends it to the client, or sends a command from the client to the TIMS server and saves the study as a DICOM file and sends it to the PACS.

This invention allows for two different types of user participants as defined herein, first is a Consultant Client and the other is a Collaborator Client. The Consultant Client communicates with the TIMS server by retrieving live streams from the streamer server, and in some cases, can capture the stream and view it. Consultant Clients, which can view streams through setting up channels on the network, having the ability to freeze frame streams, illustrate and save. However, the Consultant Client does not collaborate over the network with others. The initiator of the session or host consultant client can illustrate over the image with other consultant clients merely viewing the image and illustrations. An example of this would be a teacher illustrating a surgical procedure to students who merely watch. The Collaborator Client communicates with the TIMS server by retrieving streams from the streaming server, saving and retrieving studies to and from a PACS server, and retrieving patient information from a (DMWL). Collaborator Clients can communicate with each other through collaboration sessions. The Collaborator Client has all the features of the Consultant Client, plus the added functionality of creating illustrations and annotations, while collaborating with others in a session, saving the collaboration session as a DICOM file (eg a dcm file) and have the ability to send the file to a PACS server or other destinations.

Users or participants, viewing images from a medical modality concurrently collaborate with each other through a collaborative session. These users or participants are also known as Collaborator Clients. Two or more users can concurrently collaborate in a given session. One user can initiate the collaboration session and the other users can enter the session and actively participate in the collaborative session. The initiator can share media (such as a medical modality image) in the collaboration session with it being visible to all participants. All users can add annotations on the media using the draw control on their computer. All the annotations added by any user are available and visible to all the collaboration participants. In addition, users can add telestrating drawings, text annotations, voice annotations, and video annotations to the collaboration as well. Telestrating is defined herein as a device allowing its user to draw a sketch over the medical image. Furthermore, each participant can also use the system to chat with each other using a text chat facility. A separate text computer window box is displayed that allows for each user to instant message each other in text format in a separate window application. One feature of the present invention is that the initiator can disable the edit control of any participant, such that a particular participant will not be able to add or edit the annotation or telestration. At this point, that participant can only view the annotations made by others users. Another feature of the present invention allows the initiator to pass control of the video stream start/stop/pause functions to another participant. This control feature can be edited to enable or disable the functionality to all participants or selected participants and can be done at any time during the collaborative session.

The invention also works with personal digital assistants. Participants (PDA) clients can use these PDAs to view, consult and collaborate on DICOM images. Personal digital assistant is any small mobile hand held device that provides computing and information storage such as hand held computers, phones, media display devices with storage and palm top computers.

The principle preferred embodiment and modes of operation of the present invention have been described in the forgoing specification. The invention which is intended to be protected herein, however, is not to be construed as limited to the particular embodiments disclosed, since these embodiments are to be regarded as illustrative rather than restrictive. Variations and changes may be made by others without departing from the spirit of this invention. Accordingly, it is expressly intended that all such variation and changes which fall within the spirit and scope of the claims be embraced thereby.

BRIEF DESCRIPTION OF DRAWINGS

Other objects, features, and advantages will occur to those skilled in the art from the following description of an embodiment and the accompanying drawings, in which:

FIG. 5, shows a graphic user interface screen shot of client selecting participants to collaborate with.

FIG. 9, shows a graphic user interface screen shot of list of multiple collaboration sessions.

FIG. 12, shows a graphic user interface screen shot of administrative controls.

DETAILED DESCRIPTION

Figure 1:
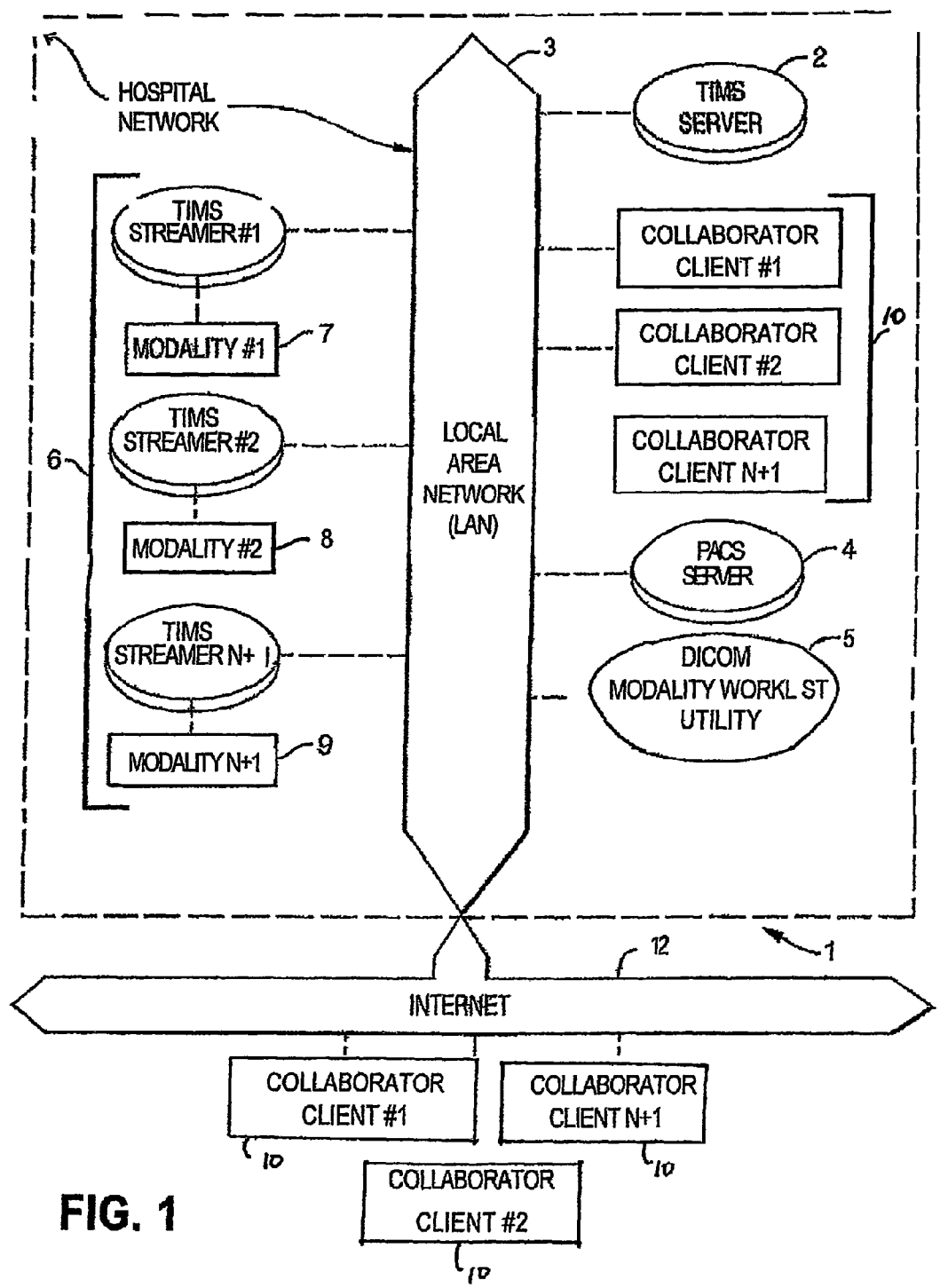
FIG. 1, shows a block diagram of the invention.
Figure 2:
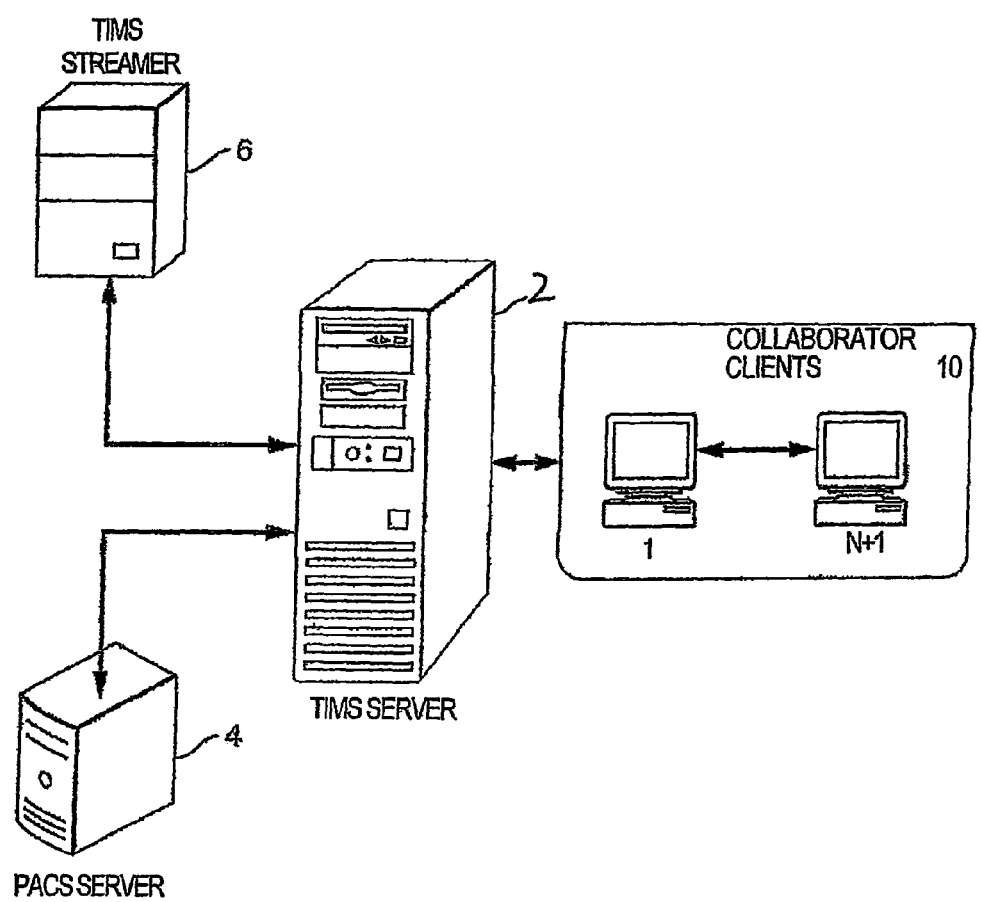
FIG. 2, shows a block diagram of a portion of the system.

A network system apparatus 1 for allowing users to concurrently communicate in real time; concurrently collaborate in real time, and concurrently consult in real time while concurrently viewing multiple sources of streaming imagers data 13 on a display screen using sketched and annotated participant client input illustrations over a streaming imagery data 13 among a group of remotely located participant clients 10.

The network apparatus system having a TIMS server 2 including associated data base in communication with a local area network 3, in some circumstances connected to and having access to a medical PACS server 4 including associated database all capable of using standard medical DICOM protocol and all having access to a DICOM modality work list server 5 including associated database providing medical patient metadata information. To collect medical images 13 the system together with at least one streaming server 6 in contact with the local area network 3 wherein the streaming server 6 is providing images to the local area network 3 as it receives images 6 from modality 7,8,9 such as but not limited to, ultrasound, fluoroscopy and video. A participant client can view medical images 13 including telesrating 22, drawings 23 and annotating notes 24 (or known as illustrations herein) over that image and saving the image with illustrations 18 on a local storage device the collaborator clients 10 all connected to a local area network 3. The local area network 13 for this illustration is a local area network within a hospital. In addition to viewing, illustration 21,22,23 and locally saving, the participant can also use the collaborative consultant client 11 option of the system. A user participant or several user participants (10,11) exchanging ideas and thoughts as Collaborative Clients 10 all connected with a local area network and all having access to the internet 12, the local area network 13 having two way communications to the internet.

This network apparatus system allows for a plurality of Consultant Clients 101 using the apparatus at the same time, as used by this system Clients can view medical images 13, and create illustrations 18 over those medical images 13 such as drawing 22 and telestrating, then storing those medical images on a local computer storage device. Different from the Consultant Client 11 where the Collaborator Clients 10 can simultaneously draw 21, telestrate 21,2 draw 22, and annotate 123 over medical images 13 the Consultant Client cannot view any other user performing the drawings, telestration and annotations that is the consultant client 11, wherein the Collaborator Clients can collaborate with each other showing the medical images 13, drawings 21, telestrations 22, and annotations 23 on all client computers at the same time and in real time. Also the Consultant Client 11 can save images locally. The network apparatus system 1 also allows users to concurrently collaborate, as defined by this system, client participants input illustrations 21,22,23,18 over streaming image among 13 a group of remotely located participant clients 10, 11. in other words, there is a plurality of collaborative clients 10 (user participants) using the system simultaneously. the plurality of collaborative clients 10, retrieve and view medical images 13, create illustrations 21,22,23 over medical images 13 such as drawing 21, annotating 23, telestrating 22 and storing medical images 13 with illustrations 21,22,23, and concurrently viewing all of the collaborative clients inputs 21,22,23 as they happen and can store all the input 21,22,23 from all collaborative clients 10 on the local computer storage device, on the PACS server 4, and on the TIMS server 2 all in DICOM format.

A method for allowing a plurality of participant clients to concurrently collaborate on medical images 13, all participant running substantially the same program on each of the client's computers storing the program on each of the client's' computers. Each participant displaying the graphic user interface output 25 of that program on their computer display. Each computer linking the client computer to the TIMS server 2 using a local area network 3. all clients, whether Collaborator Clients 10 or Consultant Clients 11 have access to the local area network 3 and interne 12. The TIMS server 2 providing authorization, authentication, identity management, security, access, and distribution privileges to each client wherein linking the client to a DICOM Modality worklist utility server 5, a PACS server 4 for viewing medical images 13, a streamer server 6. Also, the local area network 3 can be linked to the internet12.

Streaming images into a local area network 3 wherein the streaming server 6 having an associated data base in communication by directly connected to a medical image modality 7,8,9 acquiring streaming images and transmitting those images to a Collaborator Clients 10 via a local area network 3. A streaming server 5 having an associated data base, the streamer server acquires a lists 15 of available medical image modalities 7,8,915 from a local area network 3. Included in this network is a TIMS server 2 having an associated database, identifying each client and the streaming data available to each client; identifying on each client the streaming data that is available on each client's computer. Also, as part of the local area network 3 can be connected to the interne 12.

Figure 3:
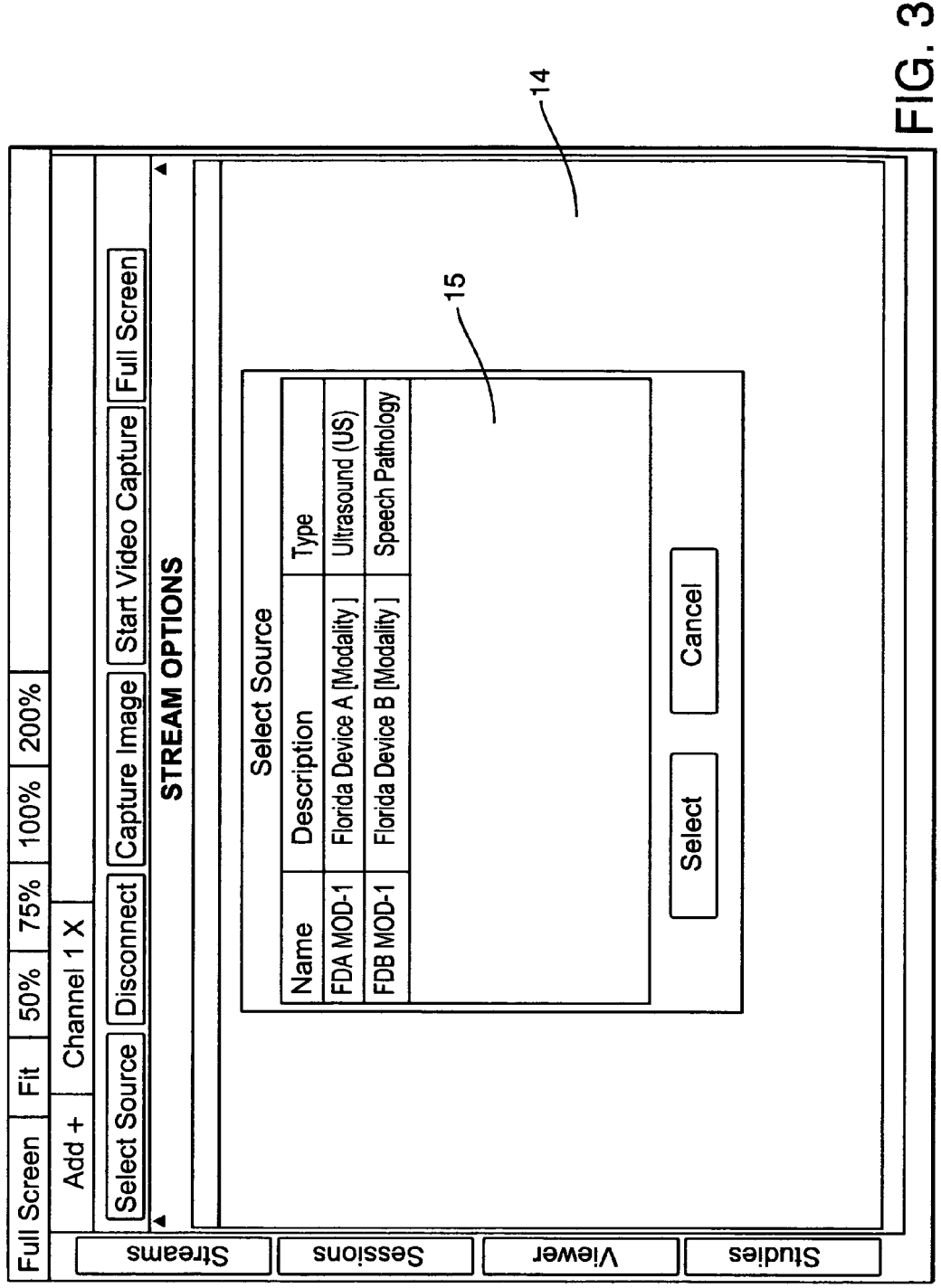
FIG. 3, shows a graphic user interface screen shot of client source select display.
Figure 4:
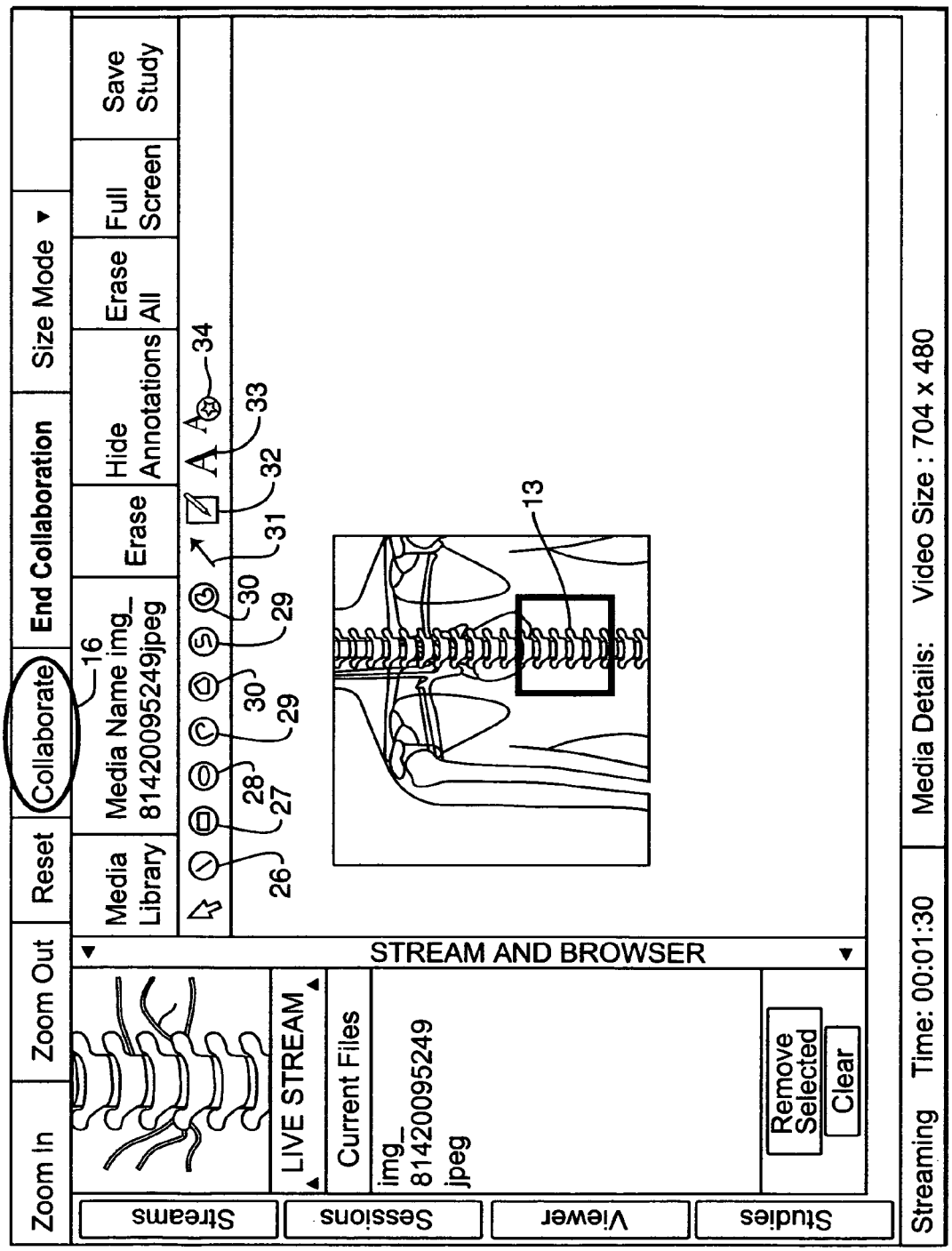
FIG. 4, shows a graphic user interface screen shot of client source image with illustration tool bar and collaborate function.

When the client wants to view medical imagery, the client selects a channel on the multi-channel source selection tab 15, 25 so he/she can initiate a collaboration session (FIG. 3). As clients are in a session, the TIMS Server 2 system is providing updates to each client's computer at a rapid frame rate so each client's computer is perceivably displaying the same image. In other words, the TIMS server 2 periodically updating any changes to each and all of the medical images to each of the participant client's computers with synchronized signals sent over the local area network 3 dynamically such that all images on all participant client computer displays are the same, including sending client's drawings 22, annotations 23, and telestrating illustrations 21,22,23 over the medical image 13 whenever a participant client 10 pauses. Thus ensuring the same frame-refresh rate is concurrently available on all participant client computers wherein each client 10 views what every other authorized client 10 in that session views. Allowing at least one client 10 to telestrate 21, draw 22, annotate 23, telestrate 22 illustrations 18 over the medical image 13 in a concurrently collaborative session wherein a client 10 is drawing 21, annotating 23, telestrating 22 input illustrations 18 over the medical image 13, the client is drawing 21, annotating 23, telestrating 22 over the medical image 13 and the computer software working over the network 13 replicating the medical image 13 along with the drawing 21, annotating 23, telestrating 23 on all other client computer displays. The image is viewed on a client computer, but remains on the TIMS server as participants creates illustrations, the file is appending to the server. Then replicating image streaming to all clients, managing client annotations, in addition to saving on the TIMS server, the user can save image locally on a computer storage device (FIG. 4), having the created illustrations 18 of all the concurrent client participants on each of the clients computers. And the software working with the computer can save and store the medical images 13 having the overlaid drawn 21 annotated 23 and teletrated 22 images in a PACS server 4 having an associated database using the DICOM format, and saving the session in a DICOM format.

Figure 5:
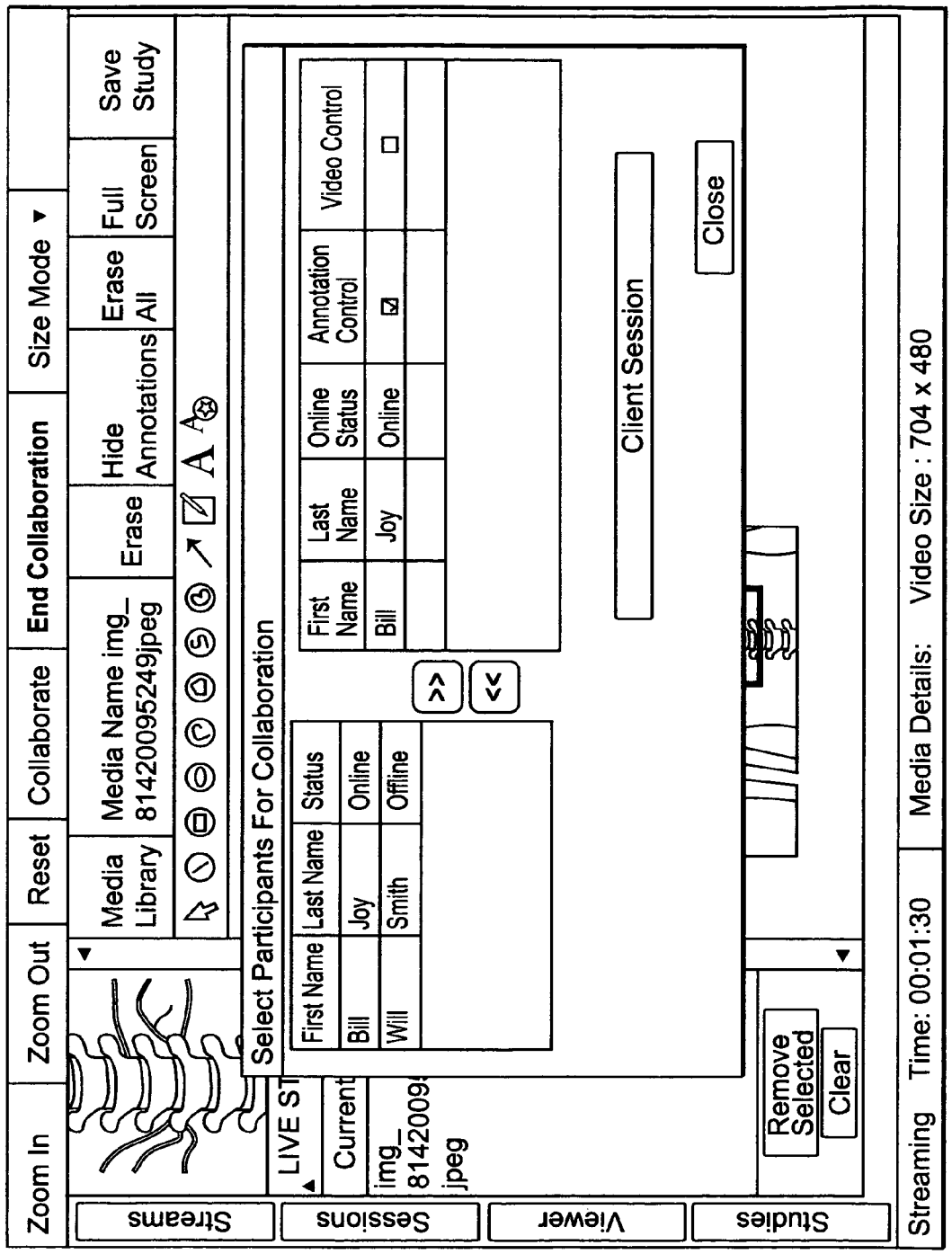
Figure 6:
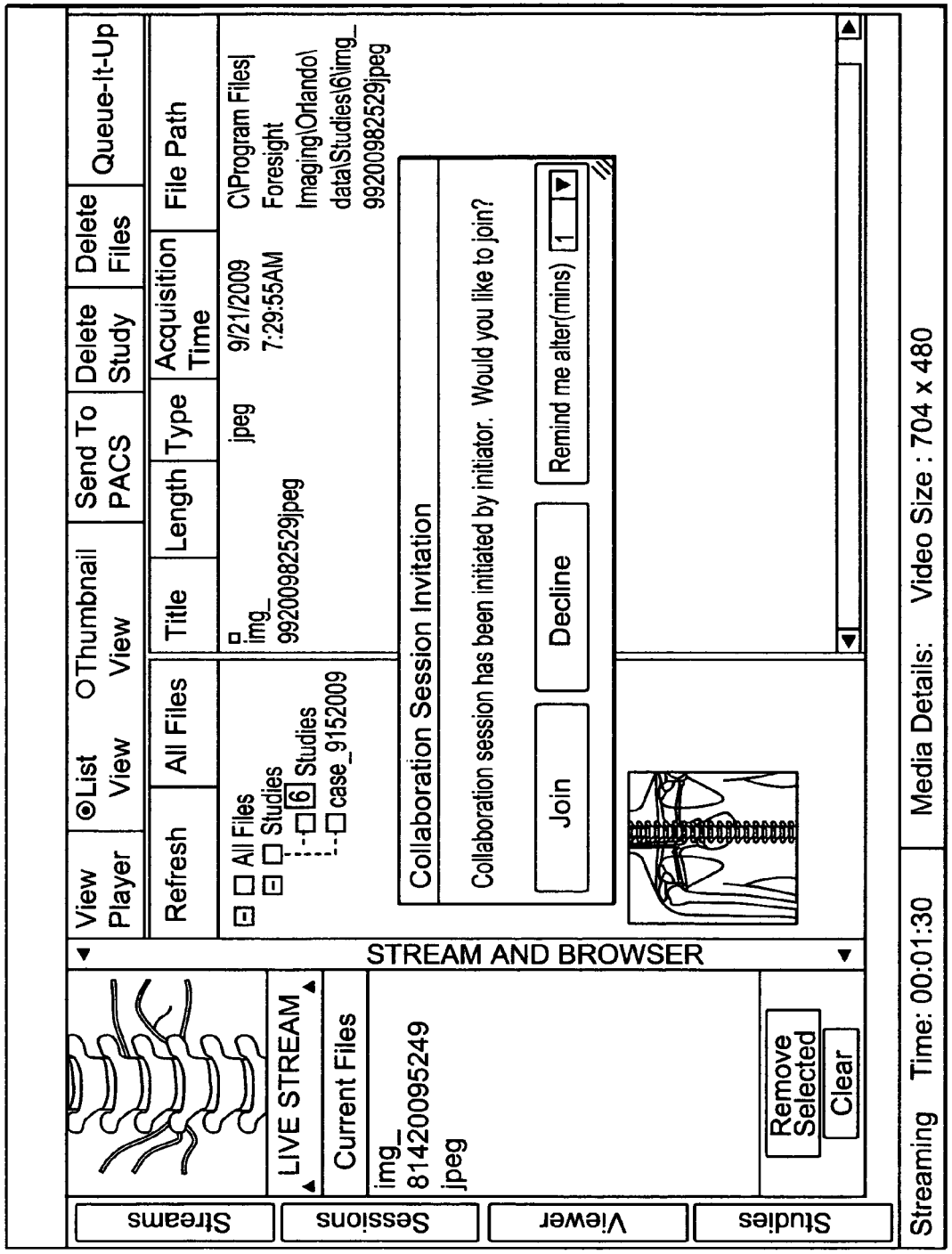
FIG. 6, shows a graphic user interface screen shot of collaboration initiated.
Figure 7:
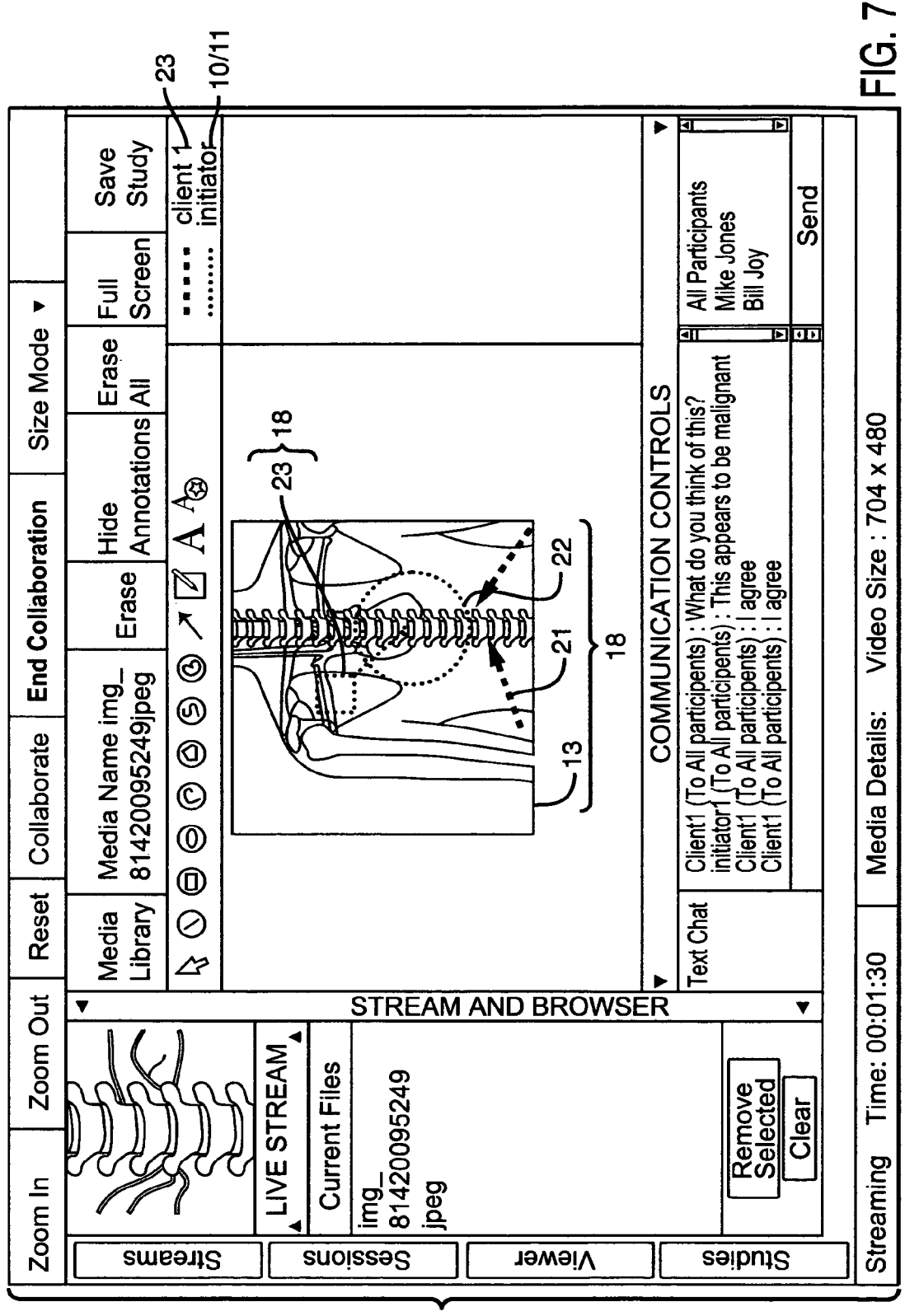
FIG. 7, shows a graphic user interface screen shot of collaboration session including medical image and illustrations.
Figure 8:
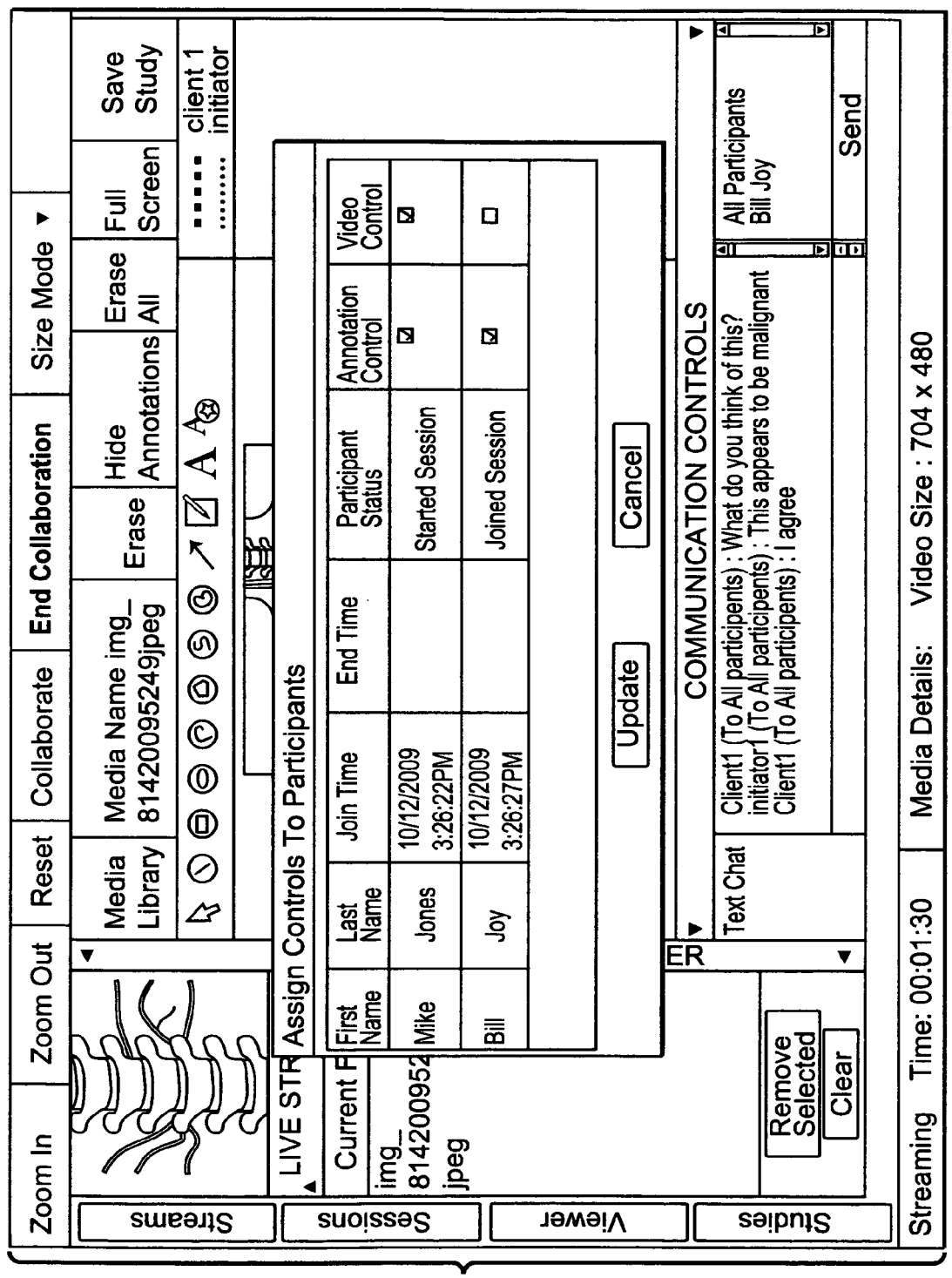
FIG. 8, shows a graphic user interface screen shot of client assignment of control to participants.
Figure 10:
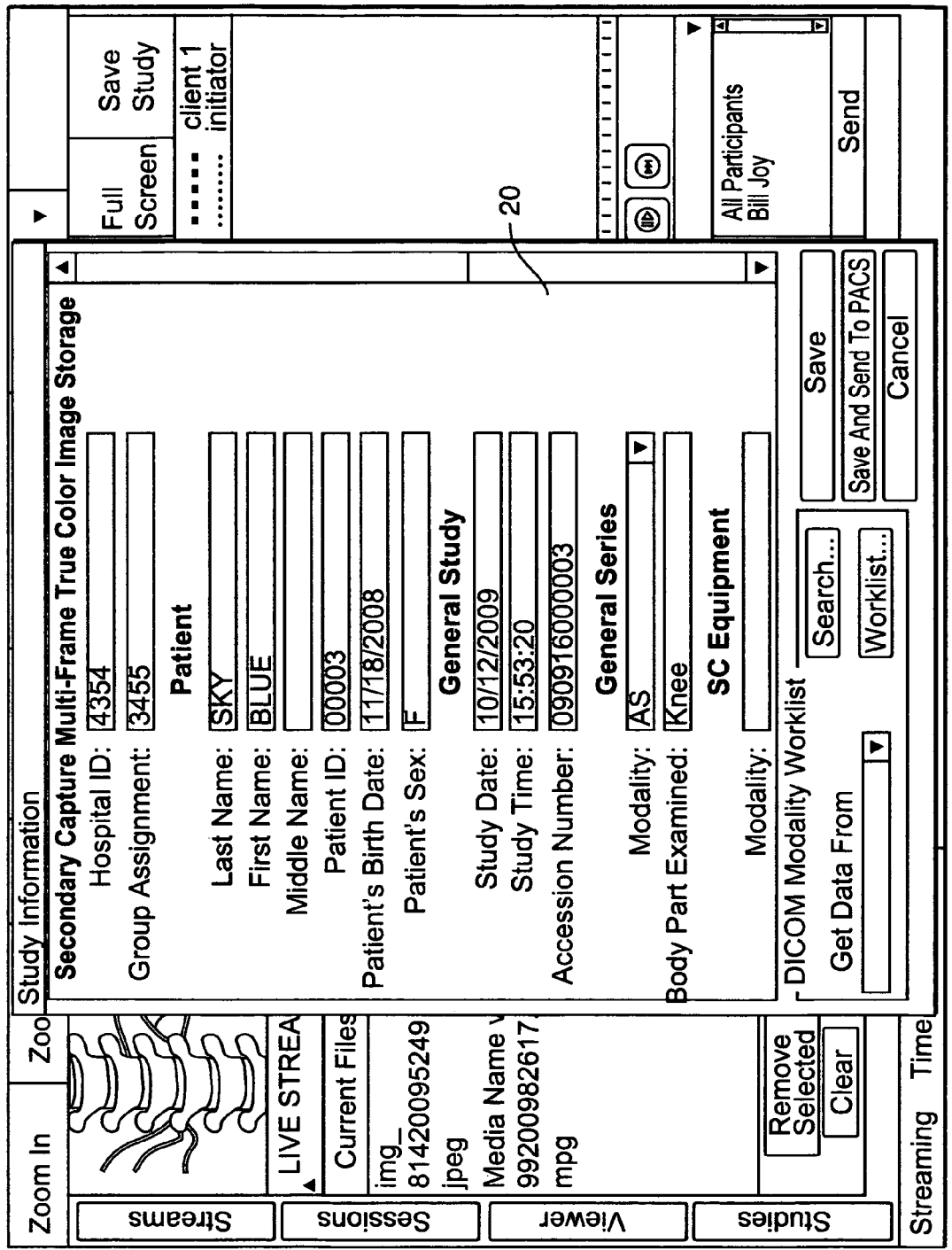
FIG. 10, shows a graphic user interface screen shot of patient image study information.
Figure 11:
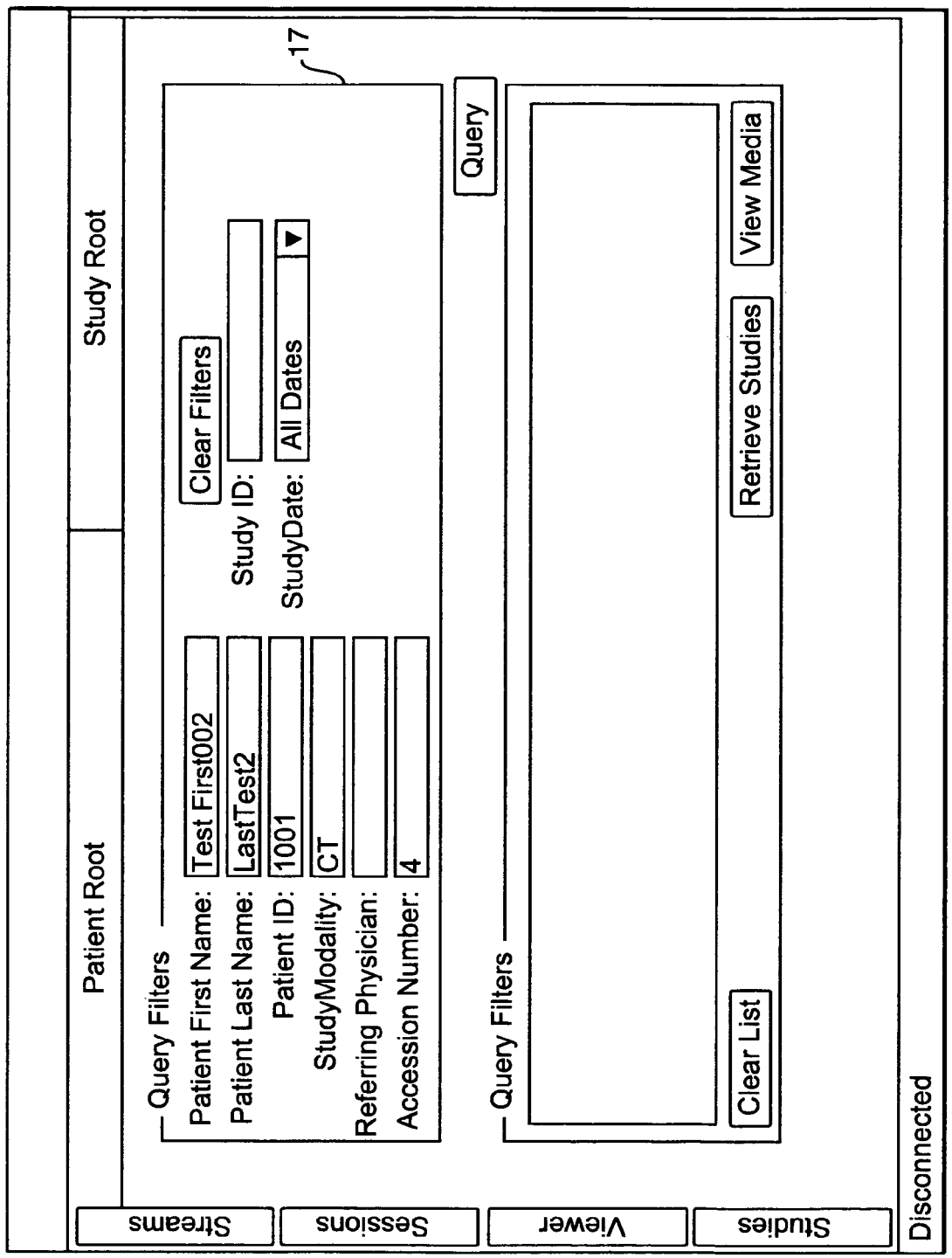
FIG. 11, shows a graphic user interface screen shot of patient database information.

The following is An illustrative example how a client would use the TIMS Collaborator™ system to collaborate on a medical image 13 and how the graphical user interface 14 is seen by the client as the client initiates and works on a collaborative session. The client participant logs onto his/her computer and accesses the local area network 3 whether the client is within the network or enters through the interne 12. Client opens the preloaded collaborator software each client then uses his/her input device such as a mouse to select or click on the streaming tab, more than one client can select the streaming tab and they will view the real time video at the same time on their computer display. After client selects the streaming tab, a list of available streams (FIG. 3) are displayed and the client participant can choose from one of those selections 15. At that time, if the client wishes to collaborate on a live streaming ultrasound image, 13 the participant can collaborate using the available functionality for the collaboration session in the viewer tab as shown in (FIG. 7) 15. In this case, one collaborator client 10 (initiator), initiates the session and collaborates with a second collaborator client, client 1, 24. the initiator can decide to request additional clients to join the collaboration session if desired (FIG. 12). In addition, a user can query the system for PACS data (FIG. 11) 17. The client can draw 21, telestrate 22 and annotate 23 over the image as he/she sees fit 18. The client participant10,11 uses prearranged computer software radio buttons located on the tool bar of the graphical user interface 25 to select what type of illustration 22,23,24 the client wishes to use to comment over the medical image 13. For instance, the participant can select to draw a line 26, a rectangle 27, an oval or circle 28, an open spline 29, or closed spline 30. The user participant 10,11 can also select a radio button for arrows 31, free hand telestrate 32 drawing free hand using movement of input device such as a computer mouse, annotate (standard alpha and numeric characters) 33, and can even annotate with a pointer arrow 34. The client host, known as the initiator, can select the collaborator radio button 16 tab to collaborate with others (FIG. 5,6). Clients can also view administrative controls such as user id, client name, and email address, roles, status and the like 19. Now, a plurality of clients can all view the same image and can all draw, telestrate and annotate (illustrations) 18 and all can see each other's work (FIG. 7), as each client draws and annotates 18 on the display, all other clients can view the drawing and annotations simultaneously. In addition, the clients can use the chat function and send to all participants, or selected participants instant messages during the session (FIG. 8). To differentiate the different illustrations and annotations apart from one another or from client to client, each client is drawing in a unique color. For example, the first clients' illustrations show up in red 22 (initiator 10, 11) and the second clients (client 24) illustrations appear in yellow and so on. One added feature of the system is that the host (client who initiated the session) can control who is invited to the session and who can illustrate (FIG. 8, 9). After the clients are satisfied with all the illustrations and agree to save the work, the image with the selected illustrations can be saved in DICOM format including having patient data within (FIG. 10) 20.

What is claimed is:

1. A network system apparatus allowing participant clients, to capture, retrieve and concurrently view both real time and archived medical images for synchronous or asynchronous communication, collaboration and consultation by one or more participant clients using participant client input illustrations over the medical images, comprising:
    a central processing unit;
    a telemedicine image management system server including at least one associated database having capability to communicate with a local area network;
    at least one telemedicine image management system streamer in network communication with a telemedicine image management system server via a local area network wherein the telemedicine image management system streamers capture one or more medical images and provide the medical images via the network communication to the telemedicine image management system server the local area network as it receives medical images from at least one source; and,
    a client software application enabling a multiplicity of participant roles, including consultant, collaborator and combinations thereof, in communication with a local area network, allowing the participant clients to input illustrations over medical images, the network system apparatus having the capability of appending the medical images periodically to the telemedicine image management system server, and saving participant client input illustrations over the medical images and sending those medical images to the telemedicine image management server for use with digital imaging and communications in medicine file structures;
    wherein one or more participant clients retrieve and view the medical images, creating illustrations over the medical images including, but not limited to drawing, annotating, telestrating and storing the medical images with the illustrations, and concurrently viewing all of the participant client's input illustrations as they happen and can save all the input illustrations from all participant clients on their local respective computer storage devices, on the telemedicine image management system server, on the picture archiving and communications system server, in a known digital imaging and communications in medicine format.

2. A network system apparatus allowing participant clients, to capture, retrieve and concurrently view both real time and archived medical images for synchronous or asynchronous communication, collaboration and consultation by one or more participant clients using participant client input illustrations over the medical images, as in claim 1 wherein, participant client input illustrations over the medical images are shared amongst a group of remotely located participant clients located on a local area network, wide area network, including world wide web, including combinations thereof.

3. A method for allowing one or more participant clients to capture, retrieve and concurrently view both real time and archived medical images for synchronous or asynchronous communication, collaboration and consultation by one or more participant clients using participant client illustrations over the medical images comprising;
    running a computer program, storing the program on each of the participant client's computers, displaying the graphical user interface output of that program on a computer display;
    linking each participant client computer to a telemedicine image management system server using a local area network, each participant client communicating with the telemedicine image management system server, the telemedicine image management system server providing permission to each participant client wherein linking the participant client to a digital imaging and communications in medicine modality worklist utility, a medical image archive server, and telemedicine image management system streamers for capturing, retrieving and concurrently viewing medical images, participant client's illustrating over the medical images, telemedicine image management system server managing all illustration file sharing wherein new participant client input illustrations are appending periodically to the telemedicine image management system server, maintaining the file on the participant client's computer, the telemedicine image management system server linking to the interne and other participant clients, wherein the images remain on the telemedicine image management system server and the participant client input illustrations are appended to that server;
    streaming image into a local area network wherein the telemedicine image management system server having associated database in communication with telemedicine image management system streamers connected directly to medical imaging modalities for acquiring one or more medical images, streaming those medical images to the local area network;
    acquiring a list of available medical image sources from the telemedicine image management system server having associated database, identifying on each participant client computer one or more sources of both real time and archived medical images available to each participant client for capture, retrieval and concurrent viewing;
    identifying on each participant client computer one or more sources of both real time and archived streaming data that is available for synchronous or asynchronous communication, collaboration, and consultation on each client computer;
    participant clients selecting from available medical image streams to initiate a synchronous or asynchronous collaboration session, providing updates to each participant client computer, telemedicine image management system server periodically updating the medical images to each of the participant client's computers with synchronized signals sent over the network such that all medical images on all participant client computer displays are the same, including sending participant client's telestrations, drawings, annotations, and input illustrations over the medical images whenever a participant client appends to the medical images allowing all participant clients to synchronize to the same frame whenever the initiator pauses the medical image streams by broadcasting the frame identifier to all participant clients wherein each participant client views the same medical image that every other authorized participant client in that session view;

allowing at least one participant client to telestrate, draw, annotate, and input illustrations over the medical images in a synchronous or asynchronous collaboration session wherein the participant client is telestrating, drawing, annotating, telestrating and inputting illustrations over the medical images, and saving participant client input illustrations over the medical images to the telemedicine image management system server for use with digital imaging and communications in medicine file structures; the telemedicine image management system server working over the network replicating the medical images along with the drawings, annotations, telestrations and input illustrations on all other participant client computer displays, and;

replicating the medical images to all participant clients, managing participant client annotations.

4. A method for allowing participant clients, to capture, retrieve and concurrently view both real time and archived medical images for synchronous or asynchronous communication, collaboration and consultation by one or more participant clients using participant client input illustrations over the medical images, as in claim 3 wherein, participant client input illustrations over the medical images are shared amongst a group of remotely located participant clients located on a local area network, wide area network, including world wide web, including combinations thereof.

5. A method for system allowing participant clients to capture, retrieve and concurrently view both real time and archived medical imagery streams for synchronous or asynchronous communication, collaboration and consultation by one or more participant clients using participant client participant input illustrations over the medical images as in claim 3 wherein; one or more participant clients retrieve and view the medical images, creating illustrations over the medical images such as, but not limited to drawing, annotating, telestrating and storing the medical images with the illustrations, and concurrently viewing all of the participant client's input illustrations as they happen and can save all the input illustrations from all participant clients on their local respective computer storage devices, on the telemedicine image management system server, on the picture archiving and communications system server, in a known digital imaging and communications in medicine format.

* * * * *